United States Patent [19]

Supersaxo et al.

[11] Patent Number: 5,470,582
[45] Date of Patent: Nov. 28, 1995

[54] CONTROLLED DELIVERY OF PHARMACEUTICALS FROM PREFORMED POROUS POLYMERIC MICROPARTICLES

[75] Inventors: Andreas Supersaxo, Basel, Switzerland; Jim H. Kou, Palo Alto, Calif.

[73] Assignee: Syntex (U.S.A.) Inc., Palo Alto, Calif.

[21] Appl. No.: 18,850

[22] Filed: Feb. 5, 1993

Related U.S. Application Data

[63] Continuation-in-part of Ser. No. 832,527, Feb. 7, 1992, abandoned.

[51] Int. Cl.$^6$ .................................................. A61K 9/52
[52] U.S. Cl. ........................ 424/489; 424/422; 424/426; 424/493
[58] Field of Search ................................. 424/489, 422, 424/426

[56] References Cited

U.S. PATENT DOCUMENTS

| | | | |
|---|---|---|---|
| 4,389,330 | 6/1983 | Tice | 427/213.36 |
| 4,675,189 | 6/1987 | Kent | 424/490 |
| 4,873,091 | 10/1989 | Jankower | 424/489 |
| 4,897,268 | 1/1990 | Tice | 424/422 |
| 4,917,893 | 4/1990 | Okada | 424/423 |
| 5,019,400 | 5/1991 | Gombotz | 424/497 |
| 5,100,669 | 3/1992 | Hyon | 424/426 |

*Primary Examiner*—D. Gabrielle Phelan
*Attorney, Agent, or Firm*—William Schmonsees; Theodore J. Leitereg; Alan M. Krubiner

[57] ABSTRACT

A controlled release pharmaceutical composition comprising a physiologically active agent dispersed in preformed porous polymeric microparticles is provided. The active agent concentration may be up to about 10% by weight to achieve controlled release. Each of the porous microparticles has a plurality of preformed pores into which active agent is loaded and from which the active agent is subsequently released to the environment of use. The compositions are capable of delivering physiologically effective amounts of active agent for at least about thirty days, which delivery may be reversibly controlled by exposure to ultrasound.

15 Claims, 8 Drawing Sheets

CONTROLLED DELIVERY OF PHARMACEUTICALS FROM PREFORMED POROUS POLYMERIC MICROPARTICLES

This application is a continuation-in-part of U.S. patent application Ser. No. 07/832,527, filed Feb. 7, 1992, now abandoned.

BACKGROUND OF THE INVENTION a) Field of the Invention

This invention pertains to controlled release pharmaceutical compositions, processes for preparing the compositions, and uses thereof.

b) Description of Related Art

The advent of genetic engineering has resulted in a proliferation of new biopharmaceuticals that are orally inactive and must be administered by subcutaneous injection or intravenous infusion. Considerable effort has been invested in techniques, e.g. passive transdermal delivery, iontophoresis, and permeability enhancement, that have the potential to overcome the barriers presented by natural biological membranes and avoid the trauma of injections. Some successes with nasal, rectal, transdermal and gastrointestinal administration have been achieved with lower molecular weight polypeptides. However, parenteral administration remains the only viable route by which sustained, controlled delivery can be achieved.

The susceptibility of peptides and proteins to proteolysis and rapid clearance from the bloodstream makes them ideal candidates for controlled delivery systems. In addition, due to the high molecular weight and hydrophilicity of proteins, transdermal diffusion is impractically slow. Furthermore, the zero-order delivery kinetics associated with most transdermal systems may not be the optimum kinetic profile because of the potential down-regulation of biological receptors; in many cases pulsed or self-regulated delivery systems may be more efficient and economical.

One class of polymer systems for controlled release of polypeptides is based on polyethylene-co-vinyl acetate (EVA). Langer et al. in *Nature* 263, pp. 797–800 (1976) have shown that a wide variety of water-soluble macromolecules can be released for weeks and months from thin EVA matrices, formed by suspending macromolecular drug powder in an organic polymer solution and evaporating the solvent. Microscopy of these polymer matrices revealed a two-phase dispersion, with domains of solid drug and polymer matrix. Mechanistic studies have suggested that the macromolecules are released from these devices by a self-diffusion process, i.e. release does not involve dissolution of the drug in EVA or swelling of the polymer bulk, but rather diffusion through aqueous channels and pores created by the dissolution of dispersed macromolecules.

The pioneering work of Kent et al., as disclosed in U.S. Pat. No. 4,675,189, provided for microencapsulation of biologically active substances in polymeric matrices. Since that invention, however, little progress has been made in the development of second generation systems designed to provide controlled release of a variety of active agents.

SUMMARY OF THE INVENTION

A controlled release pharmaceutical composition comprising a physiologically active agent dispersed in preformed porous polymeric microparticles is provided. The active agent concentration may be up to about 10% by weight. In some instances the concentration of active agent must be no greater than about 2% by weight to obtain the desired controlled release profile.

Each of the porous microparticles has a plurality of preformed pores into which the active agent is loaded and from which the active agent is subsequently released to the environment of use. The compositions are capable of delivering physiologically effective amounts of active agent for at least about thirty days.

The active agent is preferably one which is effective at the microgram, nanogram, or picogram daily level. Optionally, the compositions are implanted at the situs of use.

In one embodiment the microparticles are polymers of polylactic, polyglycolic, or copoly(lactic/glycolic) acid and the active agent is a polypeptide, preferably a highly potent polypeptide, most preferably an LHRH analog or a neurotrophic factor.

In a process for preparing the pharmaceutical compositions, the preformed porous microparticles are suspended in a solution of the active agent. Optionally, vacuum or pressure may be applied to facilitate migration of the active agent into the microparticles. After the active agent has deposited in the microparticles, they are dried, and further processed as required to obtain a stable, biologically active pharmaceutical composition.

Also provided is a process for the controlled delivery of a physiologically effective amount of an active agent to an animal or human subject by introducing preformed porous microparticles containing from about 0.0001% to about 10% by weight active agent into the subject. In some instances the amount of active agent is from about 0.0001% to about 2.0% by weight.

The release of active agent from the microparticles may be controlled by exposure to ultrasonic radiation. This ultrasonic stimulation is reversible and may be used to provide pulsatile delivery of the active agent in situ.

DETAILED DESCRIPTION OF THE INVENTION

Figure 1A:
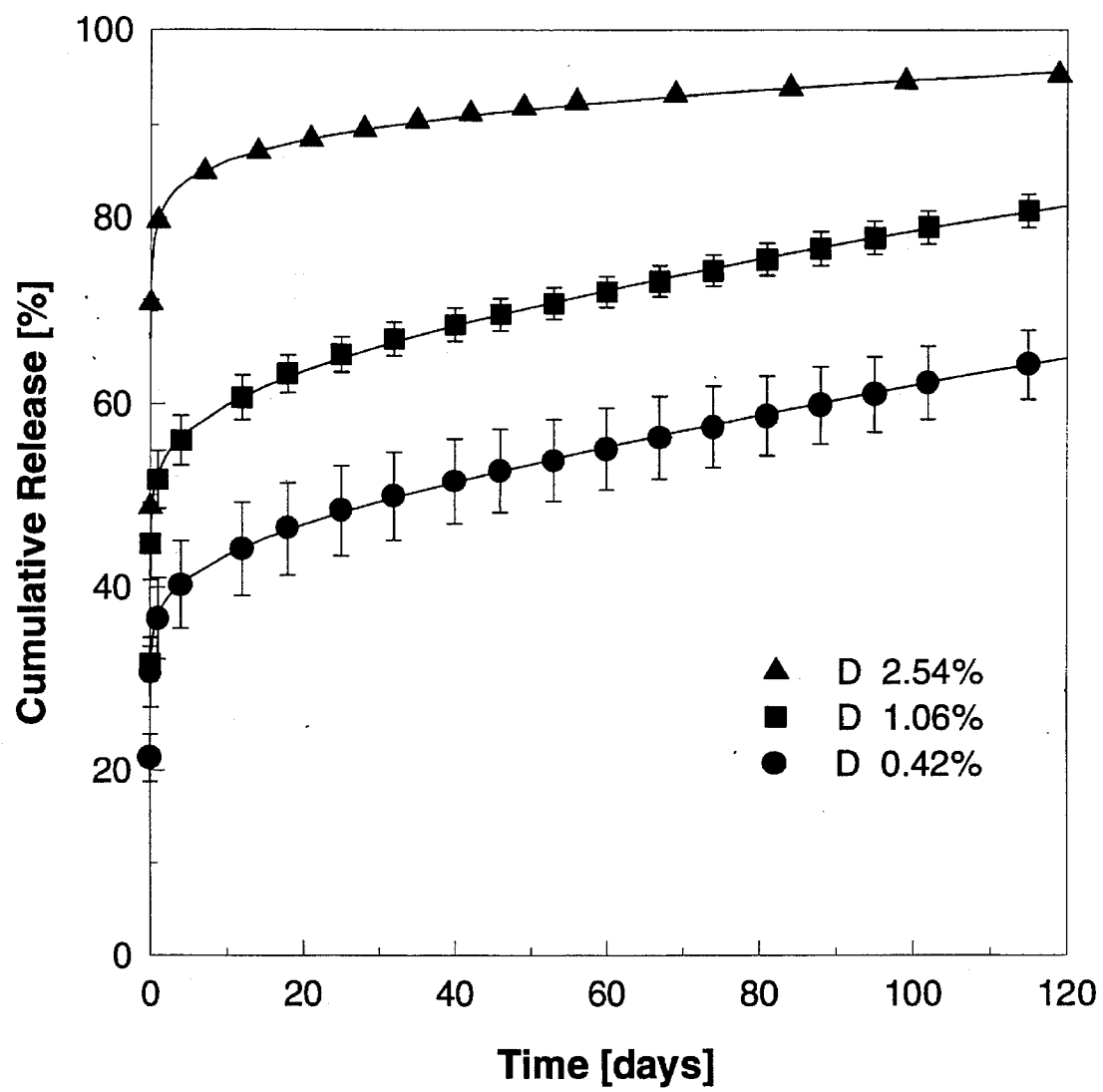
FIGS. 1a and 1b show the cumulative percent release and mass release rate profiles, respectively, for dextran-containing microparticles at various loading levels.

As used herein, the term "physiologically active agent" refers to a substance useful for the diagnosis, treatment or prevention of a human or animal disorder, or in the regulation of a human or animal physiological condition or metabolic state.

As used herein, the term "polypeptide" refers to a physiologically active agent whose active portion constitutes an amino acid sequence of varying length from about two amino acids to hundreds of amino acids, which are often referred to as peptides and proteins. Generally, the molecular weight of the polypeptides ranges between 200 and 100,000. The active portion may also contain additional derivatizing groups such as sugars or lipids.

Suitable polypeptides are exemplified by, for example, insulin, proinsulin, glucagon, parathyroid hormone, calcitonin, vasopressin, erythropoietin (EPO), renin, prolactin, human growth hormone (hGH), thyroid-stimulating hormone (TSH), corticotropin, follicle-stimulating hormone (FSH), luteinizing hormone (LH), chorionic gonadotropin, atrial peptides, interferon, tissue plasminogen activator (TPA), gamma-globulin, factor VIII, urokinase, streptokinase, the various lymphokines such as the interleukins, colony stimulating factors, and so forth. As is well known, modifications of the native amino acid sequences of the foregoing polypeptides and fragments thereof may also be used as agonists or antagonists for the native polypeptides.

Examples of native polypeptides for which altered or fragmented agonists or antagonists are available include growth hormone releasing factor, corticotropin releasing factor, luteinizing hormone releasing hormone (LHRH), somatostatin, calcitonin, thyrotropin releasing hormone, calcitonin gene related peptide (CGRP), and proteins such as enzymes, including transferases, hydrolases, isomerases, proteases, ligases, oxidoreductases, esterases, phosphatases, and various growth factors. Other proteins include vaccines derivable from proteins of viral and bacterial and parasitic infective agents.

By utilizing the method of the invention, it is possible to prepare pharmaceutical compositions suitable for parenteral administration which contain endogenous opioid agonists, such as encephalins and endorphins; hypothalamic hormones, such as gonadoliberin, melanostatin, melanoliberin, somatostatin, thyroliberin, substance P, and neurotensin; adenohypophyseal hormones, such as corticotropin, lipotropin, melanotropin, lutropin, thyrotropin, prolactin, and somatotropin; neurohypophyseal hormones; calcitropic (thyroid) hormones, such as parathyrin and calcitonin; thymic factors, such as thymosin, thymopoietin, circulating thymic factor, and thymic humoral factor; pancreatic hormones, such as insulin, glucagon and somatostatin; gastrointestinal hormones, such as gastrin, cholecystokinin, secretin, gastric inhibitory polypeptide, vasointestinal peptide, and motillin; chorionic (placental) hormones, such as choriogonadotropin and choriomammotropin; ovarian hormones, such as relaxin; vasoactive tissue hormones, such as angiotensin and bradykinin; growth and neurotrophic factors, such as nerve growth factor (NGF), ciliary neurotrophic factor (CNTF), brain derived neurotrophic factor (BDNF), glial derived neurotrophic factor (GDNF), epidermal growth factor (EGF), fibroblast growth factor (FGF), insulin-like growth factor (IGF), tumor necrosis factor (TNF), and transforming growth factor (TGF), somatomedins and urogastrone; hemophilia factors, such as blood clotting factors VIII and IX; enzymes, such as streptokinase, fibrinolysin, deoxyribonuclease, and asparaginase; and artificial or pseudo peptides, such as deferoxamine. Many other classes and specific types of peptide and protein hormones and other biologically active molecules are known, such as the LHRH analogs, nafarelin, buserelin, leuprorelin, goserelin, deslorelin, gonadorelin, triptorelin, and histrelin. Peptide and protein hormones suitable for use in the present invention are disclosed in Johannes Meienhofer, "Peptide and Protein Hormones", in *Burger's Medicinal Chemistry*, 4th ed., (part II), Wolff, Ed., John Wiley and Sons (1979).

The listing of certain polypeptides in this application is not intended to be exclusive, and it may easily be determined by conventional release studies if a particular polypeptide has sufficient biological activity to be used. A physiologically effective amount of the polypeptide is the amount of polypeptide required to produce the effect ordinarily associated with administration of that polypeptide. Typically, the polypeptide should be active at the microgram to picogram daily level. That is, the polypeptide is effective for its intended purpose when microgram to picogram amounts are delivered per day. Such polypeptides are characterized as "highly potent".

For example, the highly potent LH-RH agonist, nafarelin, is active at about 24 micrograms/day dosing. A 100 mg bolus (i.e., given rapidly at one time for immediate response) of microparticles containing about 1.0 mg of nafarelin (1% loading) could deliver 24 micrograms/day of nafarelin for about 40 days. Or, a 40 mg bolus of microparticles containing about 1.0 mg of nafarelin (2.5% loading) could deliver greater than 10 micrograms/day of nafarelin for about 50 days.

The term "controlled release" as used herein is meant to describe the phenomenon whereby the active agent is released from the microparticles to the environment of use over an extended period of time. In many instances the release profile is characterized by an initial burst, in which much of the active agent is released in a matter of hours, followed by an essentially constant, slow release of active agent from the microparticles. For some drugs, high initial burst may be desirable in order to induce a rapid, intense physiological response, followed by a period of maintenance therapy; for other drugs, low (<10%) initial burst is desirable in order to minimize side effects and avoid initial hyperreactivity, while still providing a physiologically effective dose over time. The latter objective may be achieved by use of low loading level microparticles, having on the order of 1 or 2 weight percent active agent.

The release rate may also be controlled to some extent by the co-incorporation of release rate modifying excipients and additives. Additionally, in the event the active agent is one which is deactivated by freeze drying, a cryoprotectant may be added. Generally, the amount of cryoprotectant greatly exceeds the amount of active agent.

Suitable excipients, additives, and cryoprotectants include proteins, such as serum albumin; carbohydrates, including simple sugars such as mannitol and sucrose and polysaccharides such as dextran; lipids such as 1,2-dipalmitoyl-sn-glycero-3-phosphocholine (DPPC) and 1,2-dipalmitoyl-sn-glycero-3-[phospho-rac-(1-glycerol)]sodium salt (DPPG), and mixtures thereof; and surfactants such as polysorbate 80 (Tween 80).

The cryoprotectant and the release rate controlling excipient or additive need not be the same, but may be independently selected. Selection of an appropriate excipient, additive or cryoprotectant is within the purview of the skilled artisan; representative compounds may be found in *Remington's Pharmaceutical Sciences*, 18th Ed., (Mack Publishing Company, Easton, Pa., 1990).

An important feature of this invention is the use of preformed porous microparticles for delivery of the active agent. The microparticles, which may assume a variety of shapes, generally have diameters of from about 50 to about 400 microns and are extensively permeated with a network of pores into which the active agent is introduced. In a preferred embodiment, the microparticles are microspheres. Pore sizes range from about 0.01 to about 1.0 micron in diameter with no particular distribution of shape or size required. The void volume of the microparticles may range from 20 to 90%, preferably from 30 to 80%, most preferably from 50 to 80%.

The microparticles are prepared from any suitable polymeric material, such as polyesters, polyamides, polyanhydrides, and polyacrylates. Preferably, the polymer is one which will degrade over time in the body, such as poly(lactic) acid, poly(glycolic) acid, copoly(lactic/glycolic) acid and poly[1,3-bis(-p-carboxyphenoxy)propane-co-sebacic acid]. Processes for forming such particles will be apparent to the skilled artisan and include, but are not limited to, spray drying of the polymeric material to generate substantially spherical particles or freeze drying followed by ball milling to produce randomly shaped particles. Unlike the microencapsulation processes of the art which rely upon simultaneous formation of the microparticle and incorporation of the active agent, the current invention starts with preformed porous microparticles and adds the active agent in a separate step. This approach has the advantage of avoiding exposure of the active agent to potentially denaturing solvents, temperatures, or other reaction conditions.

The active agent may be induced to migrate into the microparticles by simply equilibrating the microparticles in a solution or suspension having the desired concentration of the active agent. Suitably, the active agent may migrate into the microparticles over a period of about 15 min to about 30 hours. Either aqueous or non-aqueous solvents such as methanol, ethanol or iso-propanol may be advantageously used depending upon the choice of active agent and microparticle type. Alternatively, more aggressive techniques, such as the application of pressure or vacuum, may be employed to accelerate the migration of the active agent into the microparticles. Optionally, the microparticles may be pretreated to increase their compatibility with the active agent; for example in the case of poly(lactic) acid microparticles, it is advantageous to pre-wet them with ethanol.

After adding the active agent, the microparticles may be dried in air, under vacuum, by controlled evaporative drying, by a flowing inert gas, by freeze drying, or by such other techniques as will be apparent to the skilled artisan.

The active agent concentration in the microparticles is from about 0.0001 to about 10 weight percent, more preferably from about 0.001 to about 5 weight percent, and most preferably from about 0.001 weight percent to about 2.0 weight percent.

It is particularly surprising that in some instances controlled release for long time periods may be achieved by the incorporation of lesser, rather than greater, amounts of active agent.

One advantage of the invention is that the dried, active agent-containing microparticles may be stored indefinitely without adverse effects on the potency of the active agent. When it is desired to administer the microparticles, they may be suspended in a suitable pharmaceutical medium and administered to the subject. In one embodiment, the microparticles are implanted at the situs where the physiological effect is desired, for example, in a neoplasm. Porous microparticles which are suitable for use in the invention include, but are not limited to, Accurel® microporous polymer products (Akzo Fibers and Polymers Division, Accurel Systems, Box D-8753, Obernburg, Germany). These microparticles are microspheres having diameters of about 100 to 300 microns, void volumes of 50 to 80%, pore sizes of 0.1 to 1 micron, and a loading capacity of up to 70% by weight. The preparation of these materials is described in U.S. Pat. No. 4,645,664, issued Feb. 24, 1987, incorporated herein by reference.

Typically, it is stated there that the microspheres are prepared by dissolving finely divided polylactide (homopolymer of L-lactic acid) in phthalic acid diethyl ester. The components are mixed with stirring and heating, preferably at a temperature of about 150° to 170° for 1 to 2 hours. In case insoluble impurities are present, the hot solution is filtered. The clear solution is then slowly cooled, e.g., by allowing it to stand at room temperature. The resulting suspension consists of a crumbly mass which is collected by filtration and still contains phthalic acid diethylester depending on the concentration and quality of the polylactide used. The crumbly mass is extracted with a solvent suitable to dissolve the phthalic acid diethylester but not the polylactide. Examples of such solvents are methanol, ethanol, and isopropanol; ethanol being the preferred solvent. It is advantageous to carry out the extraction in an extraction apparatus such as a Soxhlet apparatus. The solid is collected and dried at 40° to 60° and then converted into powdery form, e.g., by passing it through a screen or mesh.

Administration

The active agent-containing microparticles of this invention can be easily administered in various dosage forms as injections and implants intramuscularly, subcutaneously, intravenously, or at an organ, joint cavity, or at a lesion.

For example, an injectable formulation of the microparticles of this invention may be dispersed in a suitable aqueous medium, optionally containing preservatives (e.g. methylparaben) and/or isotonizing agents (e.g. sodium chloride, sorbitol) or they may be suspended in an aqueous medium together with a vegetable oil (e.g. sesame oil). The dose of the controlled release composition of this invention and the selection of suitable adjuvants, carriers, and solvents will be affected by the contemplated end use and will vary depending upon the nature and amount of physiologically active agent in the microparticles, the dosage form, the desired duration of release, the recipient animal, and the purpose of the administration. A single dose of microparticles may be in the range of from about 0.01 mg to about 100 mg/kg of body weight.

This invention also provides a process for modulating the release of active agent from the microparticles by exposing them to bursts of ultrasonic radiation. The release rate of active agent is increased by as much as three orders of magnitude by exposure to the radiation. When the irradiation is terminated, the release rate returns to preirradiation levels. This process may be applied in a cyclical fashion to provide a high dose of active agent at a particular time followed by constant low dosing until it is deemed desirable to again provide the higher dose. The method may be practiced by exposure of the situs where the microparticles are located to the ultrasonic radiation.

EXAMPLES

The following Examples are presented solely to illustrate representative embodiments of the invention and should not be construed as limiting the scope of the claims in any way.

Example 1

Dextran-Containing Microparticles 1 g of Accurel® poly(L-lactic)acid (inherent viscosity 1.2, MP=184° C.) microspheres were wetted with 15 mL of 50% ethanol and washed three times with 15 mL of water. After decanting the water, the microspheres were equilibrated for 1 hour in 1 mL of aqueous solutions of [$^{14}$C]-labelled dextran (MW=10,200, 2 mCi/g, Sigma) to obtain microspheres having 2.54, 1.06, and 0.42 wt % loading. The microspheres were then filtered and freeze-dried.

The amount of active agent incorporated per unit weight of microspheres was determined by scintillation counting of the labelled active agent-containing microspheres. 20 mg of labelled active agent-containing microspheres were dissolved in 2 mL of methylene chloride and 20 mL of scintillation cocktail (Ready-Safe, Beckmann Instruments, Inc.) and the active agent concentration determined by liquid scintillation spectrometry (Liquid Scintillation Counter LS 8100, Beckmann Instruments, Inc.).

In vitro release studies were performed by rotating a 50 mg sample of the microspheres in 10 mL of phosphate buffered saline (PBS, pH 7.4) (Vanderkamp® Sustained Release Apparatus, VanKel Industries, Inc.). The receiving fluid was periodically withdrawn and the study continued with fresh buffer. The amount of active agent released was quantified by measuring the radioactivity.

Figure 1B:
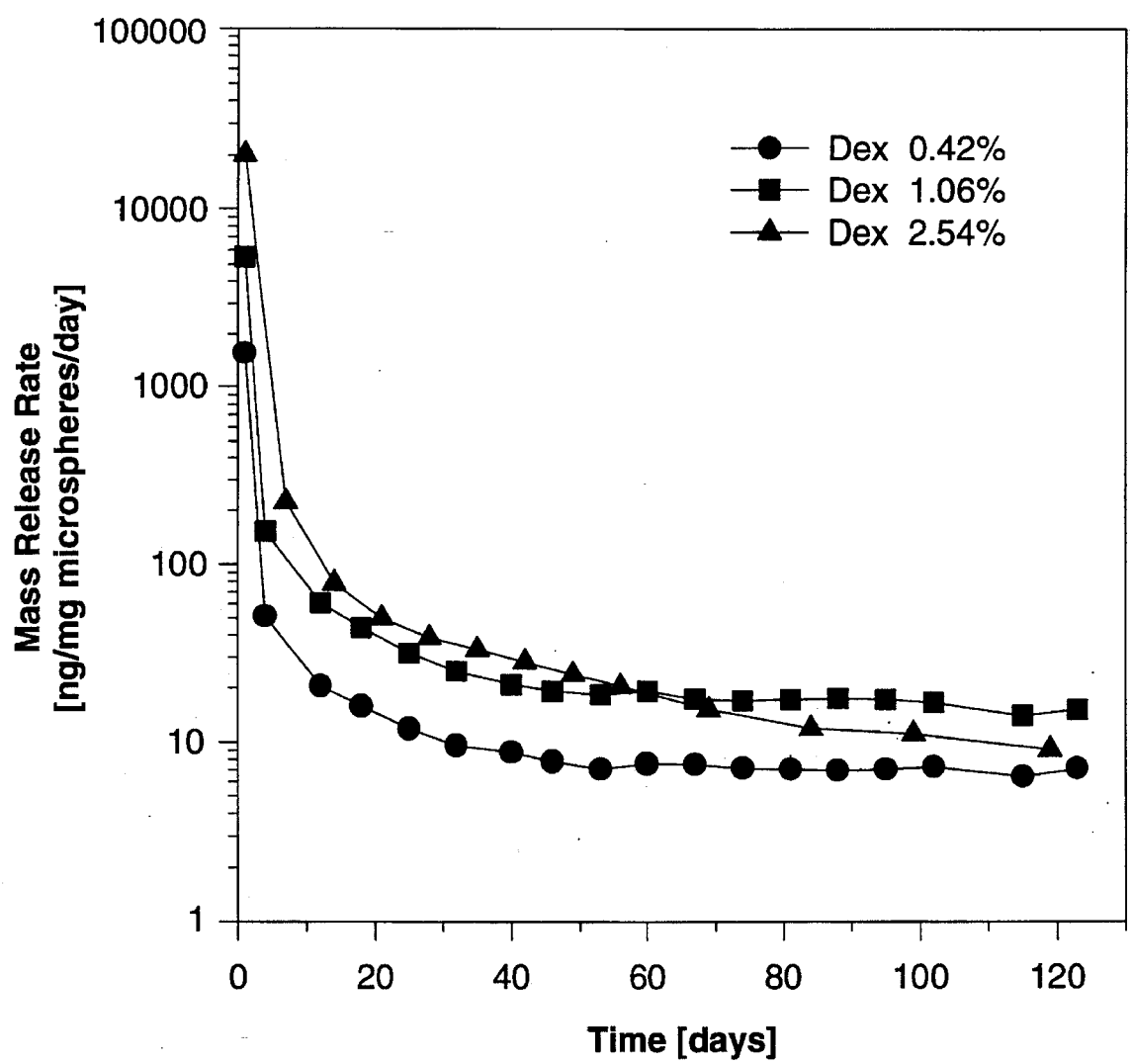

For all three preparations an initial fast release (burst) was observed. At the highest loading, approximately 80% of the active agent was released during the burst phase. However, at lower loading levels, the burst was reduced and the remaining portion was released at essentially a constant rate over several months (FIGS. 1a, 1b).

Example 2

Coincorporation of Rate-Modifying Excipients

Figure 2:
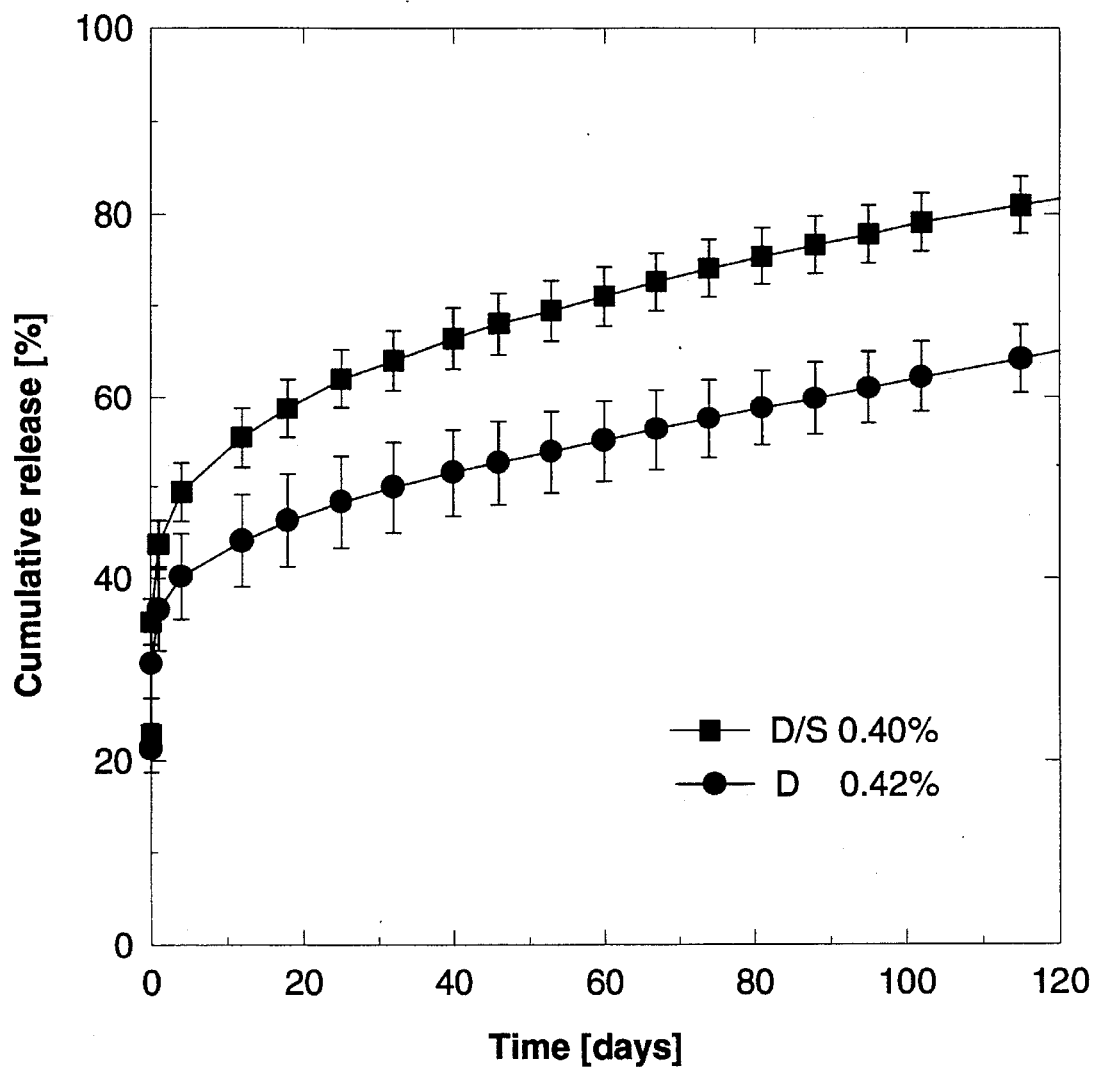
FIG. 2 compares the cumulative percent release from microparticles containing dextran plus an excipient (sucrose) to that of microparticles containing dextran only.

Following Example 1, microspheres containing 0.12 wt % dextran plus 0.28 wt % sucrose (0.40 wt % total) were prepared. FIG. 2 compares the release of the dextran from the dextran/sucrose microspheres to that from microspheres containing 0.42 wt % dextran only.

Example 3

Figure 3:
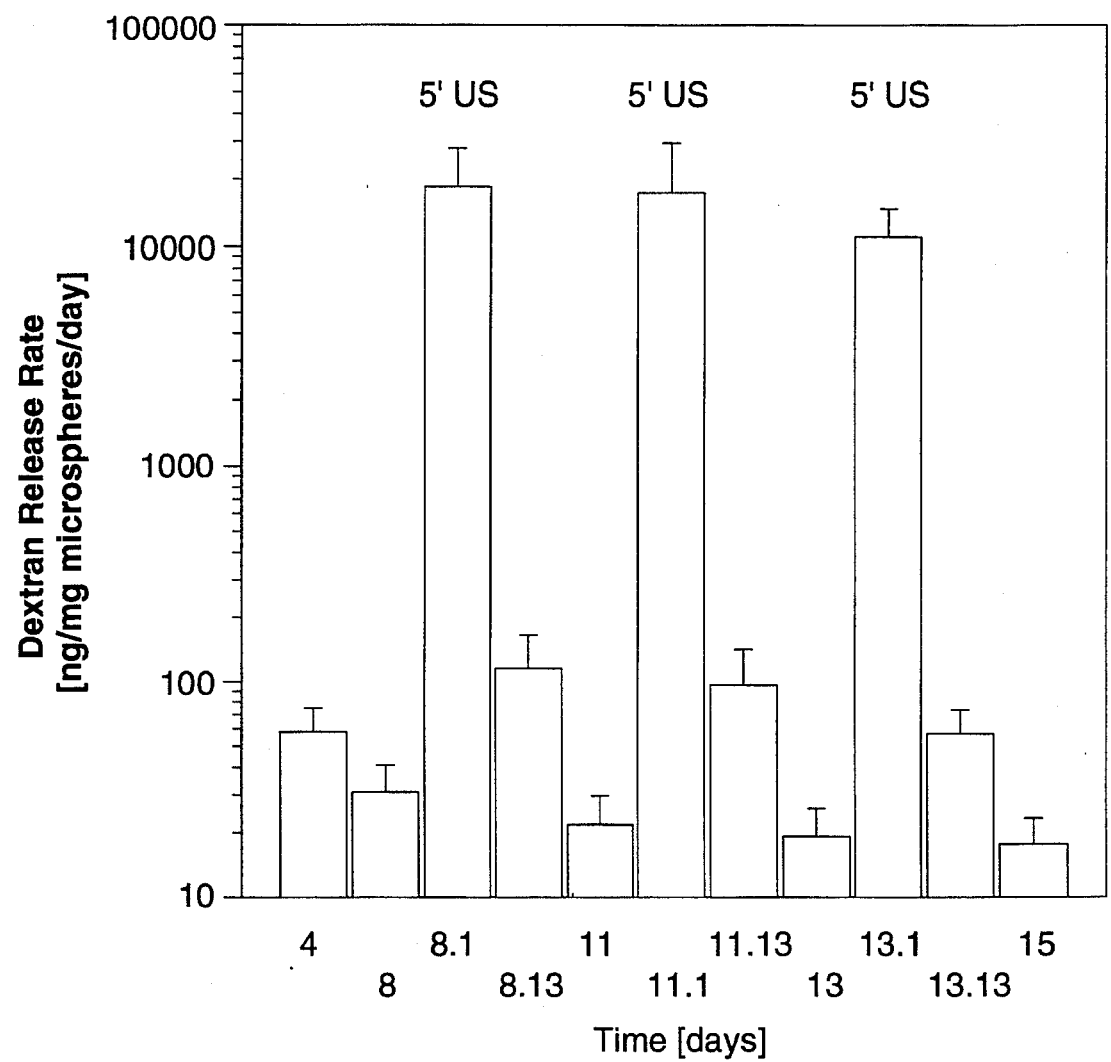
FIG. 3 shows the effect of ultrasound on the mass release rate of dextran from the microparticles.

Effect of Ultrasound 50 mg of Example 1 microspheres (0.42% dextran), preincubated in the rotating release apparatus described above, were periodically exposed for 5 min. to ultrasound. Vials containing the spheres were transferred into a glass beaker containing 250 mL water. The ultrasound device used was a Branson 2200 Ultrasonic Cleaner (Bransonic®, Branson Ultrasonics Corporation, Danbury, Conn.) generating a ultrasonic energy of ~0.3 W/cm$^2$ (personal communication, Branson Ultrasonics Corporation). After irradiation the microspheres were returned to the release apparatus. FIG. 3 demonstrates that the release of active agent from the porous microspheres can be reversibly increased by nearly three orders of magnitude by exposing them to low energy ultrasound (~0.3 W/cm$^2$). The release rate (ng/mg spheres/day) at day eight increased from 31 before irradiation to 18500 during the exposure to ultrasound and decreased thereafter within 3 hr to 511. On day eleven, before the 2nd exposure to ultrasound the release rate was 22. The release rates during the 2nd and 3rd (day thirteen) triggering periods were 17,300 and 11,000, respectively.

Example 4

In Vivo Release

Following Example 1, microspheres containing 0.21 wt % D-[1-$^{14}$C] labelled mannitol (MW 182, 60 mCi/mmol, Amersham) were prepared. Three male rats (strain CD BR Vaf+) (180–300 g) were anesthetized and 100 mg microparticles inserted with a trocar s.c. through a small surgical incision on the back of the neck. After implantation the rats were transferred to individual metabolic cages. Since mannitol is not metabolized and is excreted solely in the urine, release of the mannitol was monitored by measuring the amount excreted in the urine. The amount of radioactive mannitol excreted in the urine was quantified by counting the radioactivity present in 0.5 mL of aqueous sample emulsified in 20 mL of liquid scintillation cocktail.

Figure 4:
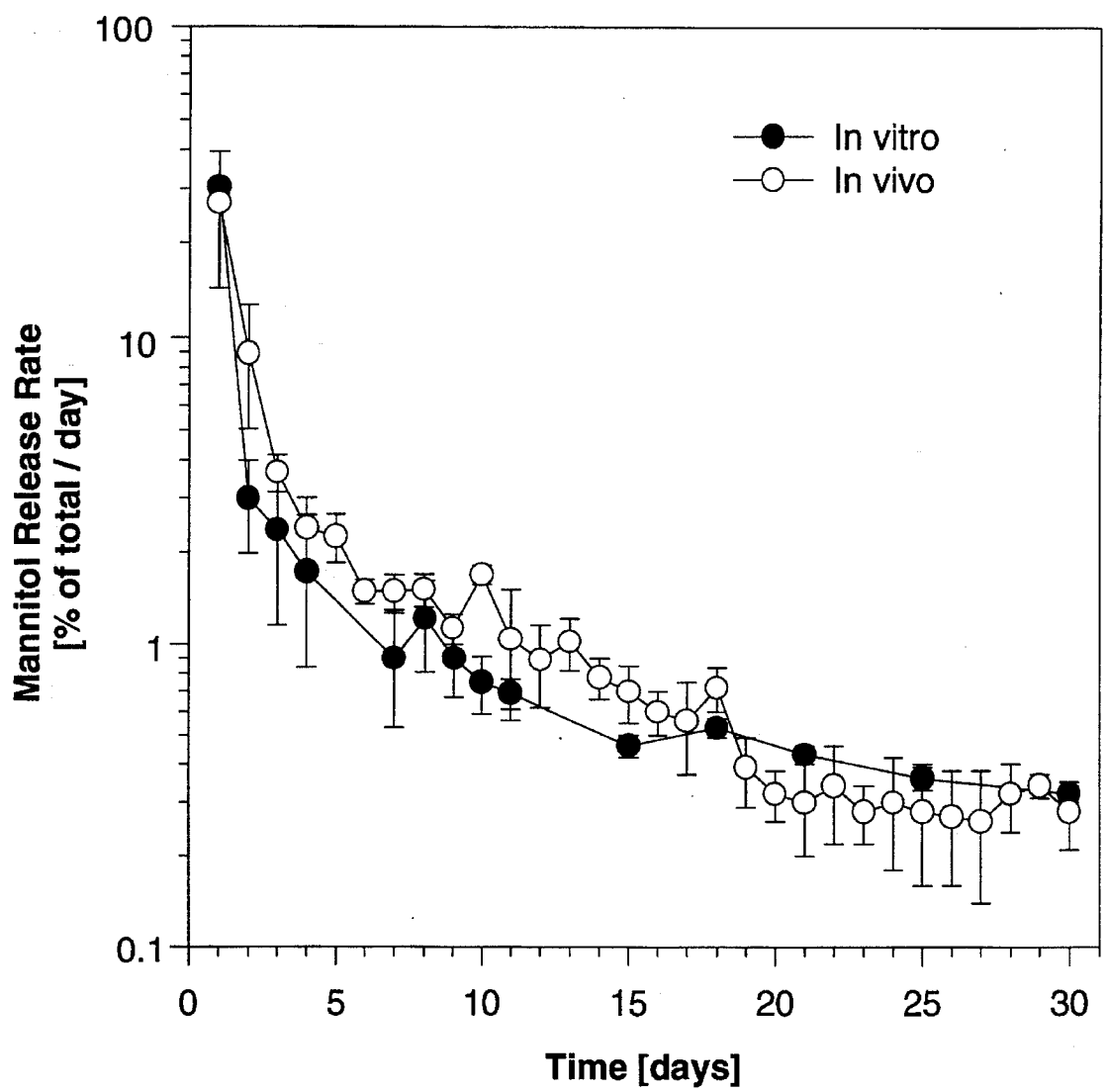
FIG. 4 compares the daily release rate of mannitol from the microparticles as determined in vivo to that determined in vitro.

The in vivo release profile of mannitol from the microspheres is illustrated in FIG. 4. After an initial burst, the remaining portion was released in a controlled manner. The release rates (% of total/day) gradually decreased from 27.0% +/–12.5% at day one (burst) to 1.7% +/–0.12% at day ten, 0.32% +/–0.06% at day twenty, and 0.28% +/–0.07% at day thirty. The implanted spheres were also tested for their in vitro release behavior and, as shown in FIG. 4, a good correlation between in vitro and in vivo release profiles was found.

Example 5

Polypeptide-Containing Microparticles

Following the procedure of Example 1, preformed porous microparticles containing up to 1.0% human growth hormone (hGH, MW=22,000) may be prepared. A 10 mg sample of such particles may be introduced into a subject and is expected to release about 500 nanograms of hGH per day for as long as 100 days.

Example 6

Nafarelin-Containing Microparticles 1 g of Accurel® poly(L-lactic)acid (inherent viscosity 1.2, MP=184° C.) microspheres were wetted with 15 mL of methanol and washed three times with 15 mL of water. The microspheres were equilibrated for 18 hours at 37° C. in 2 mL of 20% methanol/80% water solutions containing various concentrations of nafarelin acetate (Syntex Corp., Palo Alto, Calif.). The loaded microspheres were collected by filtration and dried in a vacuum oven at 40° C.

Loading Determination 50 mg of loaded microspheres were sonicated and dissolved in 2 mL of 1:1 N-methylpyrrolidone/dimethylacetamide solution. A 100 µL portion of this solution was added to 4 mL of acetonitrile and the mixture was made up to 10 mL with 0.1M pH 7 sodium phosphate. The polymer was precipitated by the addition of phosphate buffer. The solution was filtered through a disposable 0.45 µm nylon 66 membrane filter. The filtrate, after discarding the first 2 mL, was assayed for nafarelin content by an isocratic reversed phase HPLC method using a C$_8$ column. The mobile phase was 30% acetonitrile in 50 mM pH 3 sodium phosphate. The flow rate was set at 1 mL/min and the temperature was set at ambient.

The compositions of various loading solutions are summarized in Table I below. In experiments 1–3, different concentrations of nafarelin acetate were used, whereas in experiments 4–7 various excipients or additives such as dextran (mw 9300), Tween 80, and lipids were present.

TABLE I

Compositions of Loading Solutions and Resulting Loading Levels of Nafarelin Acetate in Porous Preformed Polytactic Acid Microspheres

| Exp. | Nafarelin (mg/mL) | Excipient/Additive (mg/mL) | Methanol (%) | Loading[1] (%) | (s.d.) |
|---|---|---|---|---|---|
| 1 | 100 | — | 20 | 7.10 | (0.16) |
| 2 | 10 | — | 20 | 2.43 | (0.05) |
| 3 | 2 | — | 20 | 1.41 | (0.05) |
| 4 | 10 | 10 (dextran) | 20 | 2.27 | (0.13) |
| 5 | 10 | 100 (dextran) | 20 | 2.70 | (0.09) |
| 6 | 10 | 10 (Tween 80) | 20 | 4.10 | (0.11) |
| 7 | 50 | 58:2 (DPPC:DPPG) | 0 | 8.04 | (0.05) |

[1]Numbers reported are means of three experiments with standard deviations (s.d.) in parentheses.

Drug Loading of Nafarelin

The results from experiments 1–3 show a positive correlation between the loading level and the nafarelin concentration in the loading range between 2 and 100 mg/mL. Comparisons of experiments 2 and 6 and 1 and 7 indicate that Tween 80 and lipids (DPPC/DPPG) increase the loading.

Reproducibility of Drug Loading

Three separate batches of microspheres were loaded individually using the loading solution of experiment 5 (Table I). The loading levels of these batches were determined to be 2.7%, 2.48% and 2.62%.

Example 7

In Vitro Release from Nafarelin-Containing Microparticles 100 mg of dry loaded microspheres of Example 6 were dispensed into a scintillation vial. 20 mL of fresh receiver fluid, 0.1M pH 7 sodium phosphate buffer containing 0.1% sodium azide, were added. The vial was closed with a Teflon cap equipped with a sampling port. The vial was then placed into a rack that was set into a tumbling motion. The apparatus was immersed in a constant temperature water bath at 37° C. The entire volume in the vial was sampled at fixed intervals and replaced with fresh 20 mL portions of receiver fluid. The samples were assayed by an isocratic reversed phase HPLC method using a $C_8$ column. The mobile phase was 30% acetonitrile in 50 mM pH 3 sodium phosphate. The flow rate was set at 1 mL/min and the temperature was set at ambient.

Figure 5:
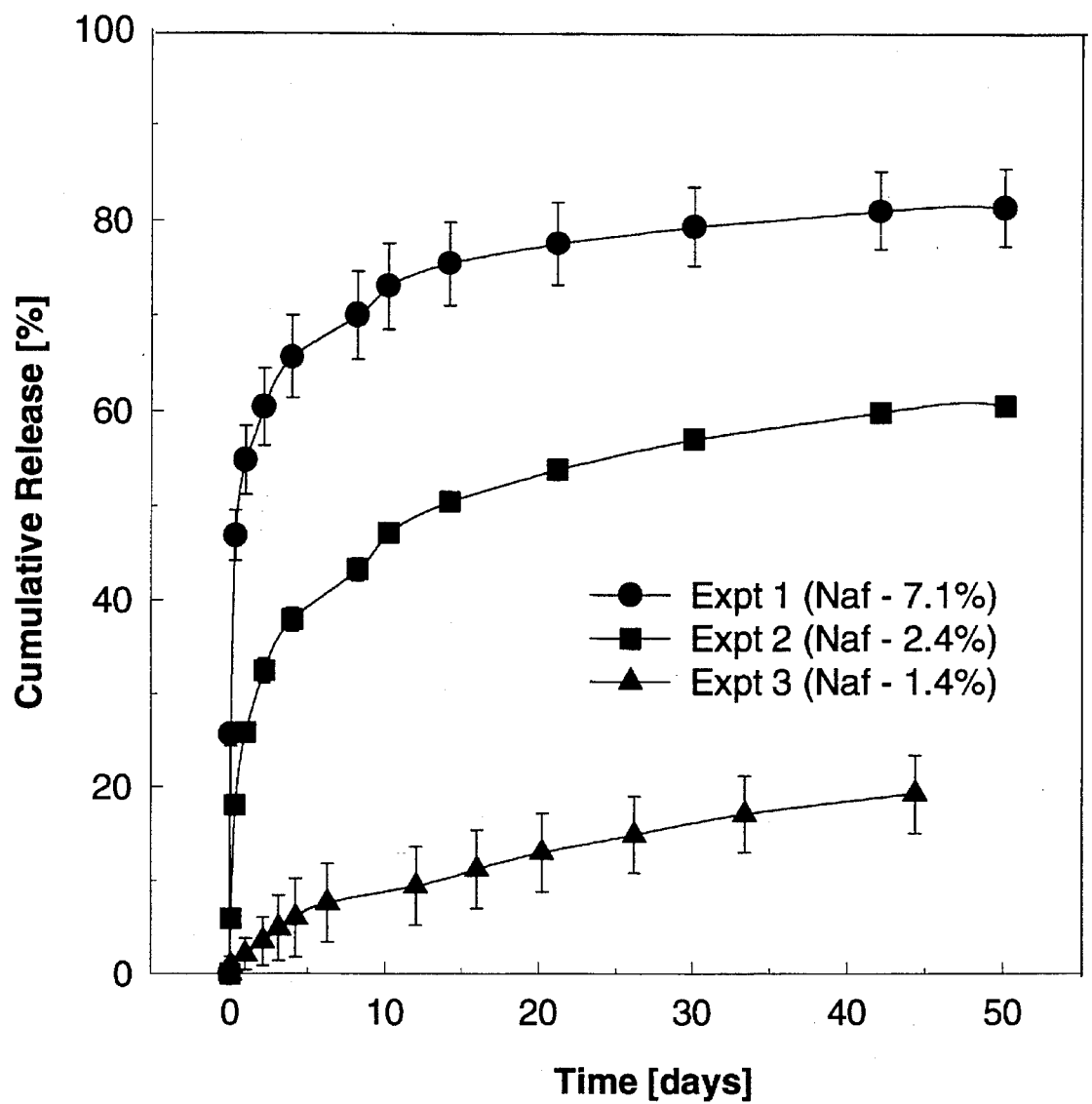
FIGS. 5 and 6 show the cumulative fractional release and mass release rate profiles, respectively, for nafarelin-containing microparticles at various loading levels.
Figure 6:
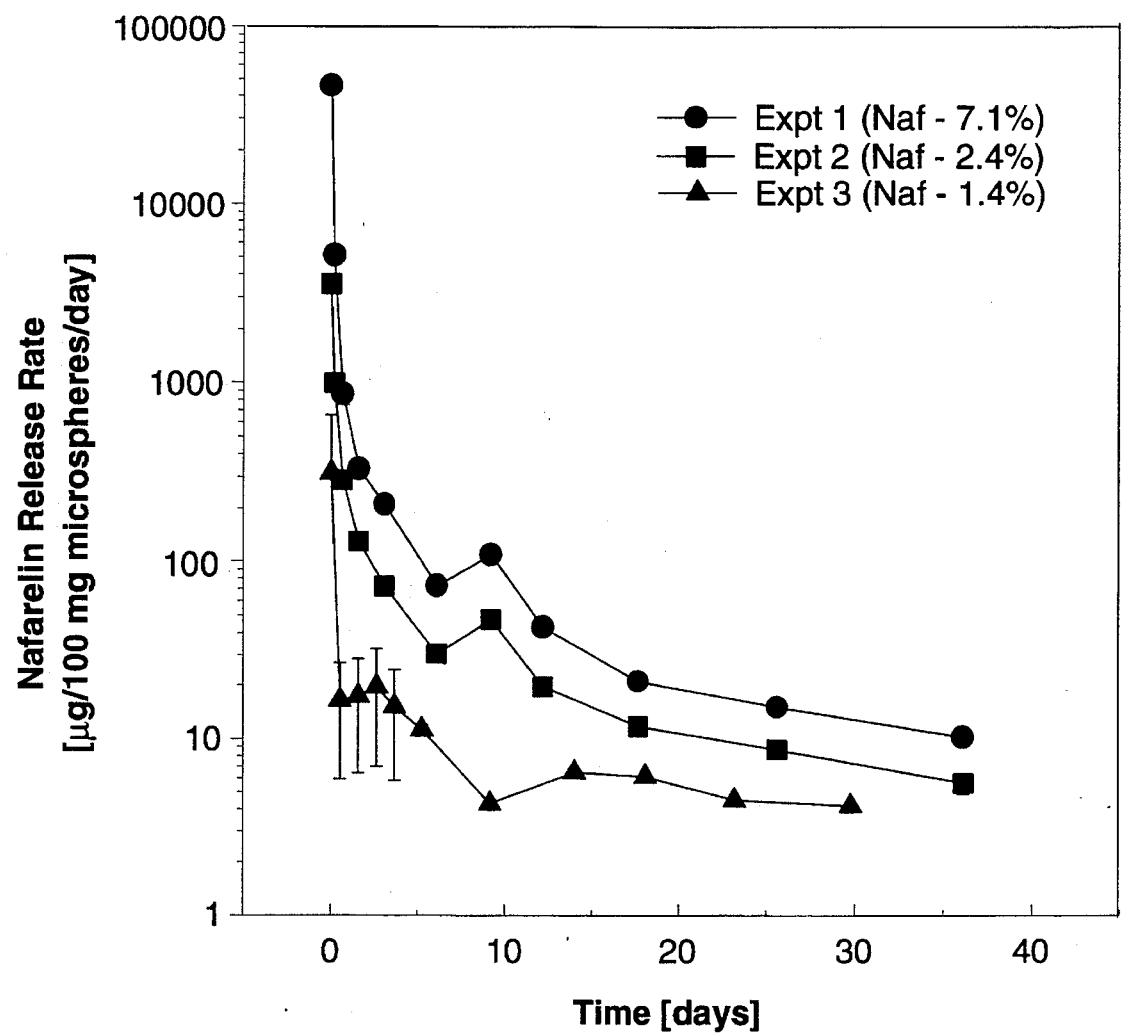
Figure 7:
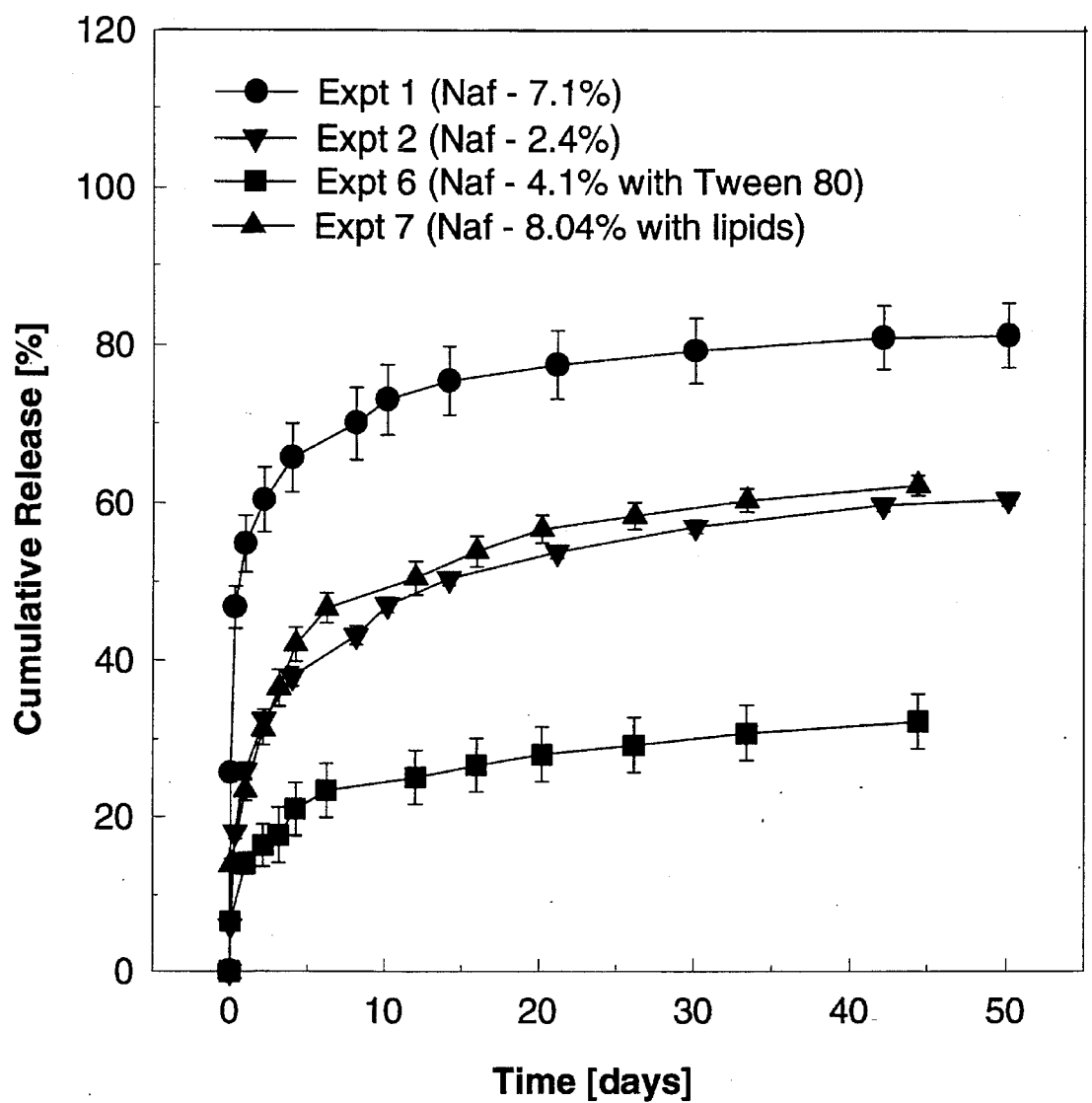
FIG. 7 shows the effect of release-modifying additives on the cumulative fractional release profiles of nafarelin-containing microparticles.

FIGS. 5–7 show drug release profiles of nafarelin from the microspheres of experiments 1–7.

Experiments 1–3 (FIG. 5) demonstrate that the drug release profiles of nafarelin are more or less biphasic, with a burst phase followed by an extended slow release phase. The one-day burst is less than 5% 25% and 55% at the loading of 14%, 2.4% and 7.1% respectively.

Experiments 1–3 (FIG. 6) further show that there is a correlation between the overall release profile of nafarelin and the loading level. The release rate of nafarelin was faster at higher loading levels. After 5 days the release rates fall into the range of 1–100 μg/day/100 mg loaded microspheres.

Experiments 1, 2, 6 and 7 (FIG. 7) show the effect of additives such as lipids (DPPC/DPPG) or Tween 80, a nonionic surfactant, on the release profile of nafarelin from the microspheres. The data suggest that both lipids (DPPC/DPPG) and surfactants retard the release of nafarelin and thus may be useful as rate-controlling excipients.

Example 8

Neurotrophic Factor Containing Microparticles

Following the procedures of Examples 1 and 6, preformed microparticles containing up to 5% nerve growth factor (NGF, MW≈26,000) or ciliary neurotrophic factor (CNTF, MW≈22,000) may be prepared. A 10 microgram sample of such particles may be introduced into a subject and is expected to release physiologically effective amounts of the active agent for several months.

What is claimed is:

1. A controlled release pharmaceutical composition comprising a physiologically active agent dispersed in preformed porous polymeric microparticles, said polymeric microparticles selected from the group consisting of polyesters, polyamides. polyanhydrides and polyacrylates, wherein said agent is present in an amount from about 0.0001% to about 2% weight, each of said porous microparticles having a plurality of preformed pores into which active agent is loaded and from which active agent is released to the environment of use, said composition being capable of delivering physiologically effective amounts of active agent for at least about thirty days.

2. A composition of claim 1 wherein said microparticles are formed from polylactic acid, polyglycolic acid, co-poly-(lactic/glycolic)acid or poly[1,3-bis(p-carboxy-phenoxy)propane-co-sebacic acid].

3. A composition of claim 1 wherein the active agent is LH-RH or an LH-RH analog.

4. A composition of claim 3 wherein said LH-RH analog is selected from the group consisting of buserelin, deslorelin, gonadorelin, goserelin, histrelin, leuprorelin, nafarelin, triptorelin, and pharmaceutically acceptable salts thereof.

5. A composition of claim 1 wherein the active agent is a neurotrophic factor.

6. A composition of claim 5 wherein said neurotrophic factor is selected from the group consisting of brain derived neurotrophic factor, ciliary neurotrophic factor, fibroblast growth factor, glial derived neurotrophic factor, and nerve growth factor.

7. A controlled release pharmaceutical composition comprising from about 0.0001% to about 2% by weight of a physiologically active agent in preformed porous microparticles of polylactic acid, polyglycolic acid, copoly(lactic/glycolic) acid or poly[1,3-bis(p-carboxy-phenoxy)propane-co-sebacic acid], said composition being capable of delivering a physiologically effective amount of active agent over a period of at least about thirty days.

8. A composition of claim 1 further comprising a release rate modifying additive or excipient or a cryoprotectant.

9. A composition of claim 1 wherein the microparticles are in the form of microspheres having diameters from about 50 to about 400 microns.

10. A composition of claim 9 wherein the microparticles comprise microspheres of poly(L-lactic) acid.

11. A process for the controlled delivery of a physiologically effective amount of an active agent to an animal or human subject which process comprises introducing preformed porous microparticles of claim 1 containing from about 0.0001 wt % to about 2 wt % active agent into the subject.

12. A process of claim 11 wherein the microparticles are implanted at a specific locus where the physiological effect is desired.

13. A process of claim 11 further comprising intermittent exposure of the microparticles to ultrasonic radiation thereby reversibly controlling the release of active agent from the microparticles.

14. A process for preparing a composition of claim 1 which process comprises:

a) mixing the porous microparticles with a solution or suspension containing an active agent for a period of time sufficient for the microparticles to absorb from about 0.0001 weight percent to about 2 weight percent of the active agent from the solution or suspension; and b) removing the solvent.

15. A process of claim 14 wherein step (a) comprises suspending the porous microparticles in a solution containing a polypeptide for a period of time sufficient to absorb from about 0.0001 weight percent to about 2 weight percent of the polypeptide from the solution.

* * * * *